(12) United States Patent
Aota et al.

(10) Patent No.: US 10,617,116 B2
(45) Date of Patent: Apr. 14, 2020

(54) CRYOPRESERVATION DEVICE

(71) Applicant: TAIYO NIPPON SANSO CORPORATION, Tokyo (JP)

(72) Inventors: Hiroki Aota, Kai (JP); Shigehiro Yoshimura, Yokohama (JP); Kouji Makino, Kawasaki (JP)

(73) Assignee: TAIYO NIPPON SANSO CORPORATION, Tokyo (JP)

( * ) Notice: Subject to any disclaimer, the term of this patent is extended or adjusted under 35 U.S.C. 154(b) by 297 days.

(21) Appl. No.: 15/557,549

(22) PCT Filed: Mar. 17, 2016

(86) PCT No.: PCT/JP2016/058581
§ 371 (c)(1),
(2) Date: Sep. 12, 2017

(87) PCT Pub. No.: WO2016/148254
PCT Pub. Date: Sep. 22, 2016

(65) Prior Publication Data
US 2018/0055043 A1  Mar. 1, 2018

(30) Foreign Application Priority Data
Mar. 18, 2015 (JP) .................................. 2015-054572

(51) Int. Cl.
*A01N 1/02* (2006.01)
*C12M 1/00* (2006.01)
(Continued)

(52) U.S. Cl.
CPC .......... *A01N 1/0257* (2013.01); *A01N 1/0236* (2013.01); *A01N 1/0242* (2013.01);
(Continued)

(58) Field of Classification Search
CPC .......... A61J 3/00; C12M 1/00; A01N 1/0236; A01N 1/0268; A01N 1/0284;
(Continued)

(56) References Cited

U.S. PATENT DOCUMENTS 5,233,844 A * 8/1993 Knippscheer et al. ..................... F25D 3/102
414/331.05
7,162,888 B2   1/2007 Shu et al.
(Continued)

FOREIGN PATENT DOCUMENTS

CN       1685185       10/2005
CN      101553701      10/2009
(Continued)

OTHER PUBLICATIONS

International Search Report for PCT/JP2016/058581 dated Jun. 7, 2016, 2 pages.

*Primary Examiner* — Gautam Prakash
(74) *Attorney, Agent, or Firm* — Nixon & Vanderhye P.C.

(57) ABSTRACT

The present invention provides a cryopreservation device that makes it possible to automatically extract an intended sample, and prevent the temperature of samples other than the intended sample from increasing. A cryopreservation device is provided, including: a cryopreservation vessel that internally accommodates a drawer configured to store vials side by side in a vertical direction in each box and has an opening communicating with a task space provided in an upper surface thereof; a drawer-raising/lowering device that raises and lowers the drawer in the vertical direction via the opening in a state where the drawer is gripped and maintains the drawer at an arbitrary height; a first stage that is provided above the cryopreservation vessel so as to be adjacent to the opening as seen in plan view and allows the box to be placed (Continued)

thereon; and a second pressing device that presses the box to move the box to the first stage.

15 Claims, 11 Drawing Sheets

(51) Int. Cl.
*A61J 3/00* (2006.01)
*F25D 25/00* (2006.01)
*B01L 7/00* (2006.01)

(52) U.S. Cl.
CPC ......... *A01N 1/0268* (2013.01); *A01N 1/0284* (2013.01); *A61J 3/00* (2013.01); *C12M 1/00* (2013.01); *F25D 25/00* (2013.01); *A01N 1/0221* (2013.01); *B01L 7/525* (2013.01)

(58) Field of Classification Search
CPC .. A01N 1/0242; A01N 1/0257; A01N 1/0221; F25D 25/00; B01L 7/525
See application file for complete search history.

(56) References Cited

U.S. PATENT DOCUMENTS

| | | |
|---|---|---|
| 2005/0260102 A1 | 11/2005 | Angelantoni et al. |
| 2008/0213080 A1* | 9/2008 | Cachelin et al. ...... B65G 1/127 414/791.6 |
| 2012/0247999 A1 | 10/2012 | Nishio et al. |
| 2013/0320833 A1 | 12/2013 | Ward et al. |

FOREIGN PATENT DOCUMENTS

| | | |
|---|---|---|
| CN | 201915085 | 8/2011 |
| CN | 203633387 | 6/2014 |
| DE | 10 2004 053 170 | 5/2006 |
| EP | 1 757 882 | 2/2007 |
| JP | 2005-143873 | 6/2005 |
| JP | 2011-019564 | 2/2011 |
| JP | 2012-215311 | 11/2012 |
| WO | WO 2004/028572 | 4/2004 |

* cited by examiner

CRYOPRESERVATION DEVICE

This application is the U.S. national phase of International Application No. PCT/JP2016/058581 filed Mar. 17, 2016 which designated the U.S. and claims priority to JP Patent Application No. 2015-054572 filed Mar. 18, 2015, the entire contents of each of which are hereby incorporated by reference.

TECHNICAL FIELD

The present invention relates to a cryopreservation device.

BACKGROUND ART

In the development of new medicines or medical basic research, biological samples, such as sperms, fertilized ova, and cells of laboratory animals, are used. Since biological samples deteriorate due to a biological action at normal temperature, it is general that the biological samples are cryopreserved by cryopreservation devices or the like. Since cryopreservation devices using liquid nitrogen can stably maintain biological samples for a long period of time, these cryopreservation devices have been widely used.

For example, Patent Literature 1 discloses a cryopreservation device that has an opening with about half the diameter of a vessel and can freely rotate an internal placement tray, as one of the cryopreservation devices using liquid nitrogen. In addition, in the cryopreservation vessel disclosed in Patent Literature 1, in order to store samples in large quantities, a plurality of samples are stored in a storage box, and a plurality of the storage boxes are stored in a case main body.

CITATION LIST

Patent Literature

[Patent Literature 1] Japanese Unexamined Patent Application, First Publication No. 2005-143873

SUMMARY OF INVENTION

Technical Problem

However, in the cryopreservation vessel disclosed in Patent Literature 1, a worker needs to load and unload the case main body in which preservation targets, such as samples, are accommodated from the cryopreservation vessel. Therefore, the burden on the worker is large, such as the need to use equipment or jigs for prevention of frostbite against low-temperature liquid nitrogen within the cryopreservation vessel. Additionally, since it is necessary to extract an intended preservation target in a state where the case main body is unloaded from the cryopreservation vessel, there is a concern that the temperature of other preservation targets accommodated within the case main body may also rise.

The present invention has been made in view of the above circumstances, and an object of the present invention is to provide a cryopreservation device that can automatically extract a preservation target, such as an intended sample, and can suppress a rise in the temperature of preservation targets other than the intended preservation target.

Solution to Problem

In order to solve the above problems, the present invention provides the cryopreservation devices of the following (1) to (16).

(1) A cryopreservation device including:
a cryopreservation vessel that internally accommodates a case configured to store preservation targets side by side and has an opening communicating with an outside provided in an upper surface thereof;
a first arm that raises and lowers the case in a vertical direction via the opening in a state where the case is held and maintains the case at an arbitrary height;
a first stage that is provided above the cryopreservation vessel so as to be adjacent to the opening as seen in plan view and allows the preservation targets to be placed thereon; and
a second arm that moves the preservation target to be located at a height adjacent to the first stage from the case to the first stage.

(2) The cryopreservation device described in (1), further including a control unit that controls at least the first arm and the second arm.

(3) The cryopreservation device described in (1) or (2), further including a third arm that moves the preservation targets placed on the first stage to the case.

(4) The cryopreservation device described in (3), further including a rotary table at a lower part within the cryopreservation vessel, in which the case is allowed to be placed on the circumference of an arbitrary circle centered on a rotary shaft of the rotary table, and the opening is located on the circumference of the circle as seen in plan view.

(5) The cryopreservation device described in (4), in which two or more of the openings are provided on an upper surface of the cryopreservation vessel so as to be adjacent to a direction orthogonal to a direction from the case side toward the first stage side, the rotary table allows the case to be placed on the circumference of each of two or more arbitrary concentric circles centered on the rotary shaft of the rotary table, and the openings are located on the circumference of each of the concentric circles as seen in plan view.

(6) The cryopreservation device described in (5), in which the first arm, the second arm, the third arm, and the first stage are movable in the direction orthogonal to the direction from the case side toward the first stage side.

(7) The cryopreservation device described in any one of (1) to (6), further including a second stage provided opposite to the first stage across the opening at a position adjacent to the opening, as seen in plan view, above the cryopreservation vessel.

(8) The cryopreservation device described in (7), in which the first stage and the second stage are movable in a pair in the direction orthogonal to the direction from the case side toward the first stage side.

(9) The cryopreservation device described in (7) or (8), in which the first stage and the second stage adjacent to the opening as seen in plan view support the case when the case is raised or lowered in the vertical direction via the opening.

(10) The cryopreservation device described in any one of (1) to (9), further including an identification device that identifies the preservation targets placed on the first stage.

(11) The cryopreservation device described in any one of (1) to (10), in which the preservation targets are accommodated in vials, and the vials are stored in a box side by side in two dimensions in the vertical direction.

(12) The cryopreservation device described in (1), further including a third arm configured to move the preservation targets placed on the first stage to the case, a tip part of the third arm is provided with a plurality of pressing arms, the second arm is provided with one pressing arm, the one pressing arm is movable in a direction orthogonal to a direction from the case toward the second stage, and the first stage is further provided with a holder having a space into which the plurality of pressing arms are inserted.

(13) The cryopreservation device described in (12), in which the holder is provided with a partition plate configured to partition the space into which the plurality of pressing arms are inserted.

(14) The cryopreservation device described in (12), further including a guide that restricts a positional deviation when the case is raised and lowered in the vertical direction, and the guide has a first guide located up along a lifting and lowering direction of the case, and a second guide located below the first guide.

(15) The cryopreservation device described in (14), further including a second stage provided opposite to the first stage across the opening at a position adjacent to the opening, as seen in plan view, above the cryopreservation vessel, the first guide is attached to the first arm, and the second guide is attached to the second stage.

(16) The cryopreservation device described in (13), in which a tip part of the partition plate is provided with a taper.

Advantageous Effects of Invention

The cryopreservation device of the present invention include the cryopreservation vessel that internally accommodates the case configured to store the preservation targets side by side and has the opening communicating with the outside provided in the upper surface thereof, the first arm that raises the case in the vertical direction via the opening in a state where the case is held and maintains the case at the arbitrary height, the first stage that is provided above the cryopreservation vessel so as to be adjacent to the opening as seen in plan view and allows a preservation target to be placed thereon, and the second arm that moves the preservation target to the first stage.

In this way, since the first stage is provided so as to be adjacent to the opening as seen in plan view, only an intended preservation target can be extracted onto the first stage by the second arm without pulling up the entire case from the cryopreservation vessel when the preservation target, such as an intended sample, is extracted from the cryopreservation vessel by the first arm. Hence, the intended preservation target can be automatically extracted, and a rise of the temperature of preservation targets other than the intended preservation target can be suppressed.

DESCRIPTION OF EMBODIMENTS

Figure 1:
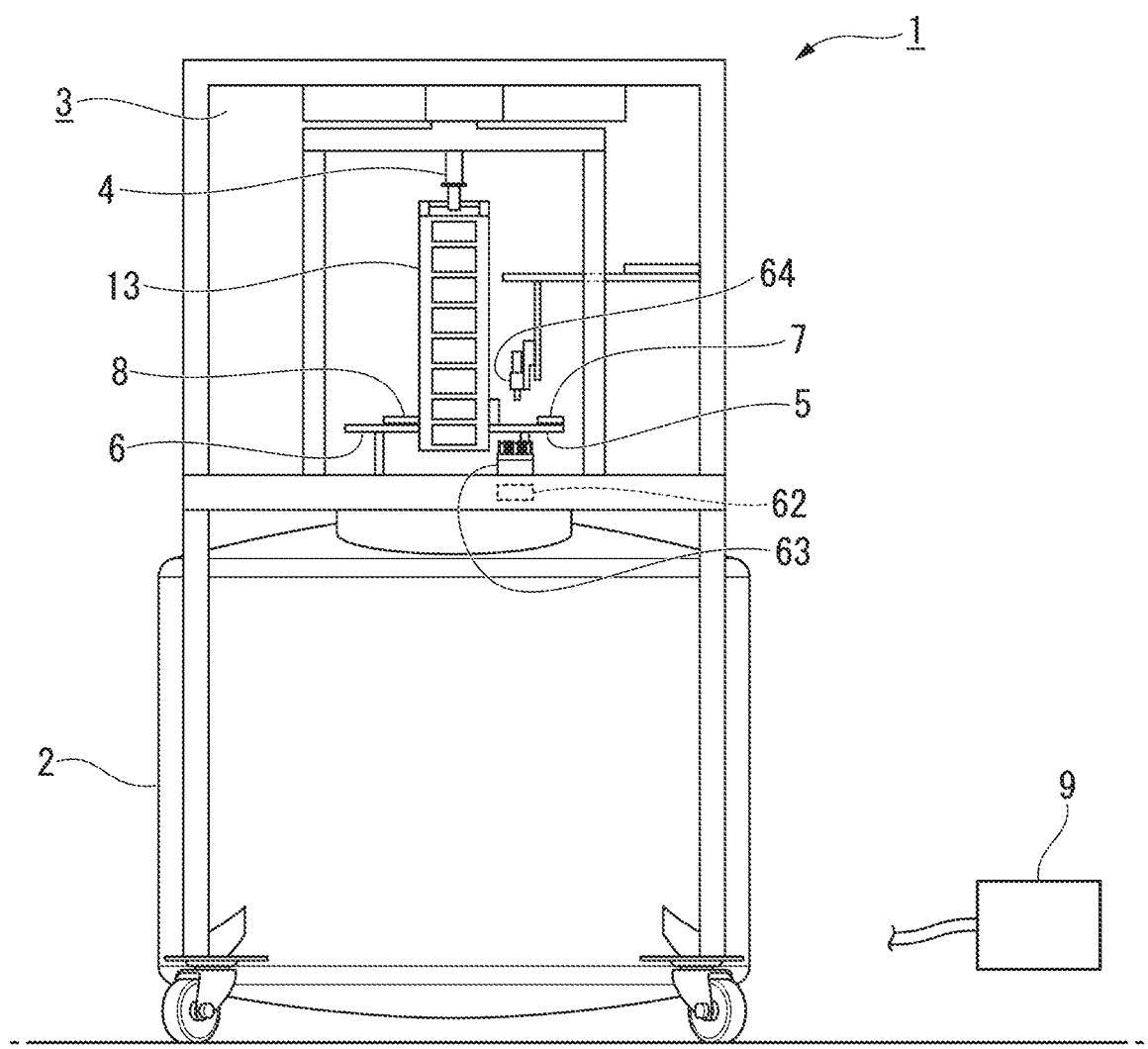
FIG. 1 is a side schematic view illustrating a cryopreservation device according to a first embodiment according to the present invention.

Hereinafter, a cryopreservation device of a first embodiment according to the present invention will be described in detail. In addition, in the drawings to be used in the following description, characteristic portions may be illustrated in an enlarged manner for convenience in order to make characteristics easily understood, and the dimension scales or the like of respective constituent elements are not necessarily the same as actual dimension scales.

First Embodiment

<Cryopreservation Device>

First, the cryopreservation device of the first embodiment according to the present invention will be described, referring to FIGS. 1 to 8. FIG. 1 is a side schematic view illustrating the cryopreservation device 1 of the first embodiment to which the present invention is applied. As illustrated in FIG. 1, the cryopreservation device 1 of the present embodiment roughly includes a cryopreservation vessel 2; a drawer-raising/lowering device (first arm) 4, a first stage 5, a second stage 6, a first pressing device (third arm) 7, a second pressing device (second arm) 8 and a control device (control unit) (not illustrated) that controls at least the drawer-raising/lowering device (first arm) 4 and the second pressing device (second arm) 8, which are provided in a task space 3; and an input/output device 9 for management configured to perform input and output of loading and unloading information of a vial or a drawer (a case) to and from the control device, which is provided outside thereof.

The cryopreservation device 1 of the present embodiment independently drives the drawer-raising/lowering device 4 and the second pressing device 8 using the control device (not illustrated), thereby automatically extracting an intended biological sample preserved within the cryopreservation vessel 2 and reducing a rise in the temperature of a biological sample other than the intended biological sample.

Figure 2:
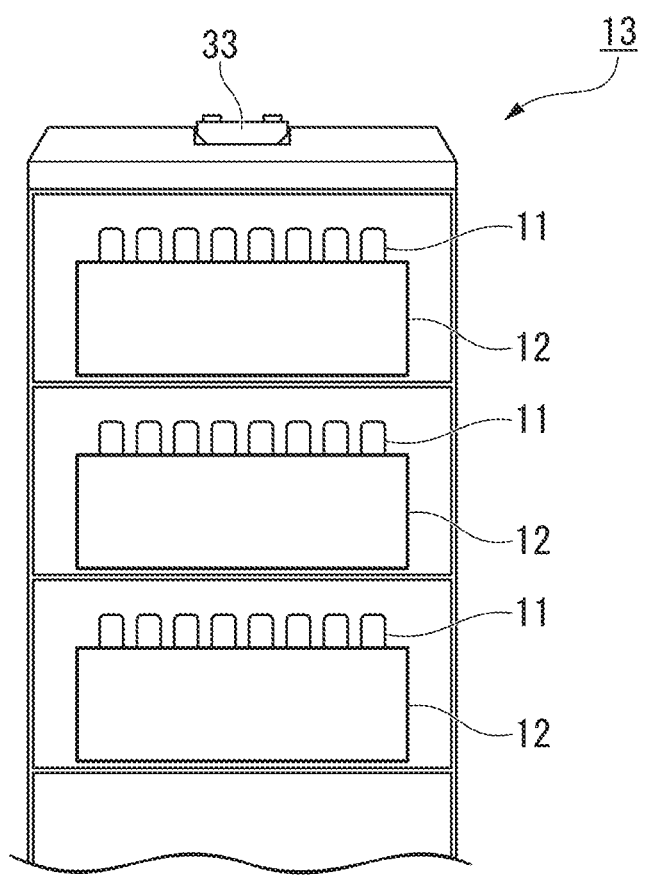
FIG. 2 is a side schematic view illustrating a drawer in the cryopreservation device of the first embodiment according to the present invention.

In addition, as illustrated in FIG. 2, in the cryopreservation device 1 of the present embodiment, a plurality of the vials (preservation targets) 11 are arrayed and stored within boxes (units) 12, and the boxes 12 are stored side by side in a vertical direction in the drawer (case) 13 (hereinafter may be referred to as a "Z-axis direction").

The vials 11 are cylindrical vessels configured to directly accommodate samples, such as biological samples. As long as the vials 11 directly accommodate the samples, such as the biological samples, and withstand a low temperature within the cryopreservation vessel, vessels made of various materials, such as resin and glass, can be used and are not particularly limited.

The boxes 12 are boxes configured to store the vials 11. Although the boxes 12 are not particularly limited, bottom surfaces of the boxes 12 may be open so that the plurality of vials 11, such as 48 vials or 96 vials, can be stored side by side in two dimensions and bar codes pasted on the bottom surfaces of the vials 11 stored in the boxes 12 can be read by a bar code reader to be described below.

The drawer 13 is provided with a shelf configurated to store the boxes 12 side by side in the Z-axis direction. The drawer 13 can be gripped by the drawer-raising/lowering device 4 and can be raised and lowered in the Z-axis direction. The drawer 13 is not particularly limited as long as it is possible to store the boxes 12 and to be raised and lowered in the Z-axis direction by the drawer-raising/lowering device 4.

As illustrated in FIG. 1, the cryopreservation vessel 2 is provided at a lower part of the cryopreservation device 1 of the present embodiment. The cryopreservation vessel 2 is a vessel configured to accommodate the drawer 13 therein and cryopreserve the drawer.

Figure 3:
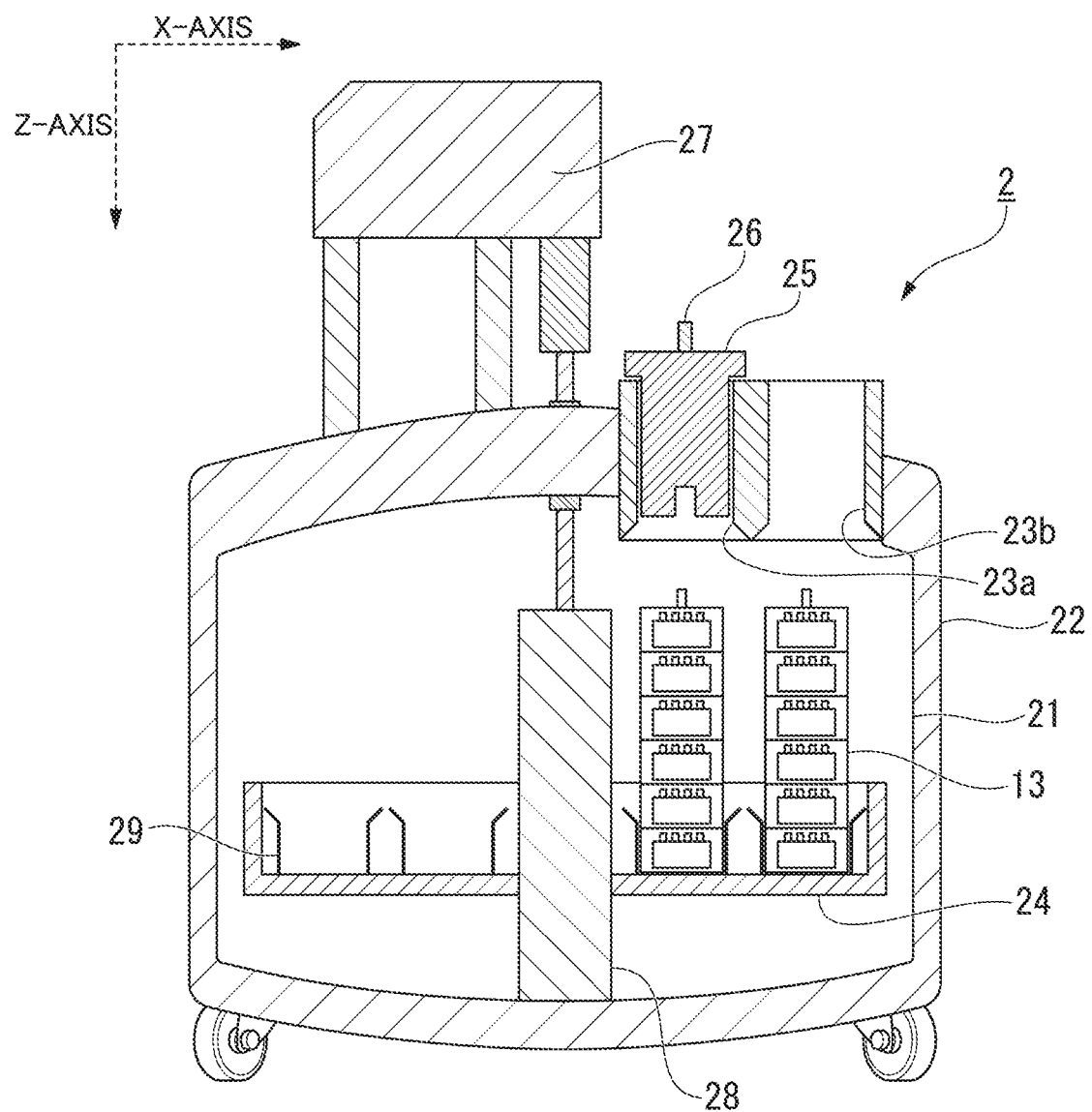
FIG. 3 is a sectional schematic view of a cryopreservation vessel in the cryopreservation device of the first embodiment according to the present invention, as seen from the side.

FIG. 3 is a sectional schematic view of the cryopreservation vessel 2 in the cryopreservation device 1 of the first embodiment according to the present invention, as seen from the side.

As illustrated in FIG. 3, the cryopreservation vessel 2 is a vacuum double-insulation vessel which has a double structure made of stainless steel or the like and formed by an inner tank 21 and an outer tank 22 and in which an air gap between the inner tank 21 and the outer tank 22 is a vacuum. Hence, by filling the inside of the inner tank 21 with a low-temperature liquefied gas, such as liquid nitrogen, the inside thereof can be kept in a low-temperature state. For example, a gaseous phase portion inside the inner tank 21 can be kept at −150° C. or lower by filling the liquid nitrogen up to the vicinity of a lower part of the inner tank 21, specifically, up to under a drawer table (rotary table) 24 to be described below.

An upper surface of the cryopreservation vessel 2 is provided with two openings 23a and 23b. An internal space of the cryopreservation vessel 2 and the task space 3 communicate with each other via each opening 23a or 23b.

The two openings 23a and 23b are provided so as to be adjacent to each other in a radial direction of the drawer table (rotary table) 24 to be described below. Here, a direction in which the two openings 23a and 23b are aligned adjacent to each other is referred to as an "X-axis direction".

The opening area of each opening 23a or 23b is approximately equal to the area of the drawer 13 as seen in a plan view. For this reason, when the boxes 12 are conveyed from the drawer 13 in the task space 3, the boxes 12 can be prevented from erroneously falling into the cryopreservation vessel 2 from the opening 23a or 23b.

Each opening 23a or 23b allows a cap 25, which blocks the opening, to be installed therein. Here, in FIG. 3, a case where the cap 25 is provided in the opening 23a to block the opening and the opening 23b is not provided with the cap 25 will be described as an example. By providing the cap 25 in each opening 23a or 23b, the opening is blocked. Therefore, a rise in temperature within the cryopreservation vessel 2 can be suppressed.

Materials for the cap 25 are not particularly limited as long as the materials have heat-insulating characteristics, and, for example, foamed urethane resin or the like may be used.

An upper surface of the cap 25 is provided with a gripping part 26. Although the shape of the gripping part 26 is not particularly limited as long as it is easy to grip the gripping part 26 when the cap 25 is attached to and detached from each opening 23a or 23b, a shape capable of being gripped by the drawer-raising/lowering device 4 to be described below is preferable. As long as the gripping part 26 is capable of being gripped by the drawer-raising/lowering device 4, the cap 25 can be automatically attached to and detached from each opening 23a or 23b by raising and lowering the drawer-raising/lowering device 4 in the Z-axis direction.

Figure 4:
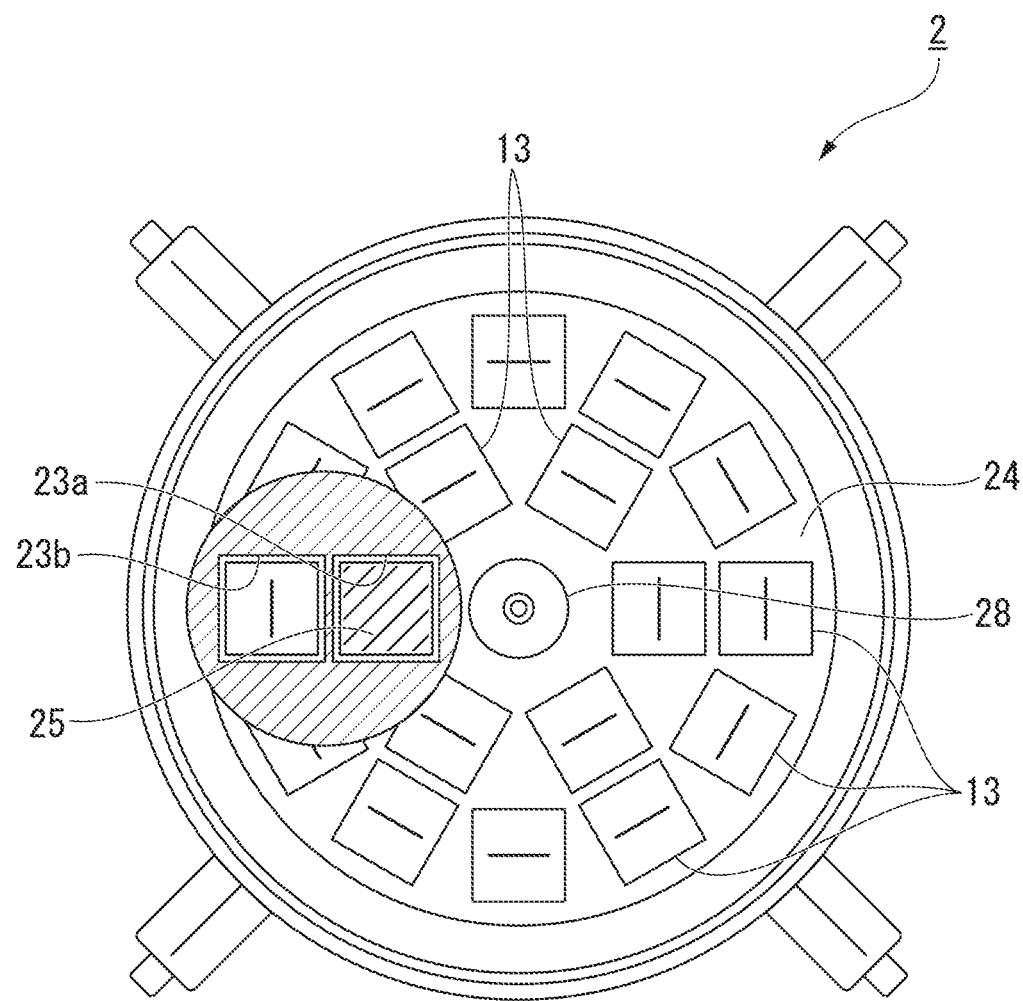
FIG. 4 is a sectional schematic view of the cryopreservation vessel in the cryopreservation device of the first embodiment according to the present invention, as seen from above.

As illustrated in FIGS. 3 and 4, a lower part within the cryopreservation vessel 2 is provided with the drawer table 24 configured to place the drawer 13 thereon. The drawer table 24 is configured so as to be capable of being rotated about a rotary shaft 28 by a motor 27 that is provided outside the cryopreservation vessel 2 and is combined with a central axis 28 of the drawer table 24.

Additionally, as illustrated in FIG. 4, a plurality of the drawers 13 are capable of being placed on the circumference of each of two arbitrary concentric circles centered on the rotary shaft 28 on the drawer table 24. In addition, as seen in plan view, the respective openings and the respective concentric circles are aligned with each other such that the openings 23a and 23b are located on the respective circumferences of the concentric circles.

Accordingly, when an arbitrary drawer 13 is extracted, the arbitrary drawer 13 can be moved so as to be located immediately below the opening 23a or the opening 23b by rotating the drawer table 24.

Additionally, as illustrated in FIG. 3, a drawer guide 29 having a tapered shape of which an upper end widens is provided on the drawer table 24 so as to correspond to a position where each drawer 13 is placed. By providing the drawer guide 29, each drawer 13 can be fixed so as to be placed at a predetermined position. Accordingly, when the drawer table 24 is rotated, the position of each drawer 13 can be prevented from deviating on the drawer table 24. Additionally, a tapered part of the drawer guide 29 can correct the positional deviation when the drawer 13 is lowered.

Figure 5:
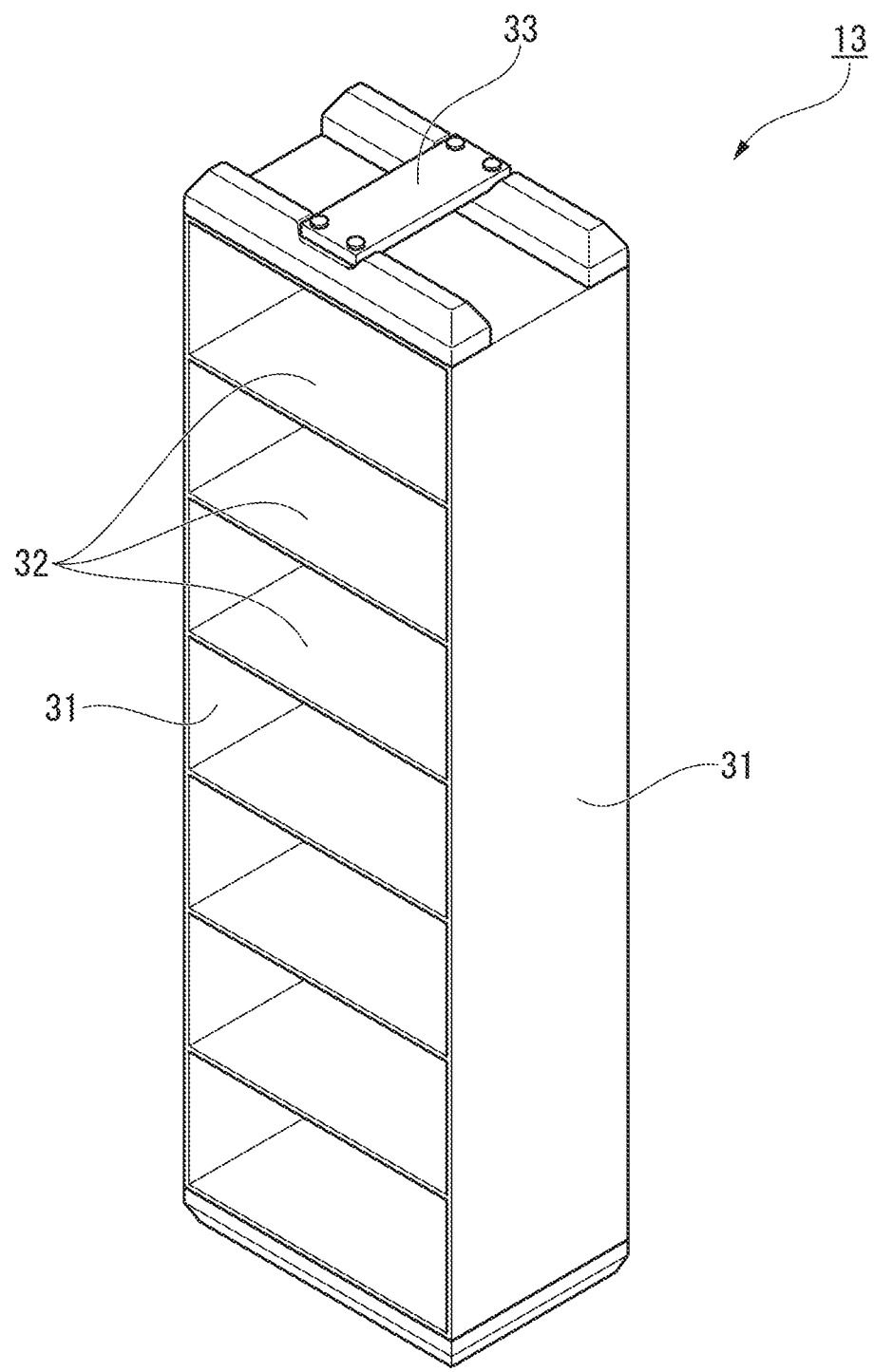
FIG. 5 is a perspective schematic view illustrating the drawer in the cryopreservation device of the first embodiment according to the present invention.

As illustrated in FIG. 5, the drawer 13 is constituted by a pair of vertical plates 31 and 31 used as side surfaces, and a plurality of floor plates 32 provided between the vertical plates 31 and 31. Accordingly, a shelf that is continuous in the Z-axis direction is provided, so that the boxes 12 can be stored on each shelf. Additionally, since at least one side surface orthogonal to the pair of vertical plates is open, the boxes 12 are capable of being taken in and out.

When each drawer 13 is placed on the drawer table 24, in a case where the drawer 13 is raised by the drawer-raising/ lowering device 4 to be described below, the drawer is placed such that the open side surface faces the first stage 5 side.

An upper surface of the drawer 13 is provided with a gripping part 33. Although the shape of the gripping part 33 is not particularly limited as long as the drawer 13 can be raised and lowered in the Z-axis direction, a shape capable of being gripped by the drawer-raising/lowering device 4 to be described below is preferable. As long as the gripping part 33 is capable of being gripped by the drawer-raising/ lowering device 4, the drawer 13 can be automatically loaded into and unloaded from each opening 23a or 23b by raising and lowering the drawer-raising/lowering device 4 in the Z-axis direction.

As illustrated in FIG. 1, the task space 3 is provided above the cryopreservation vessel 2, and communicates with the cryopreservation vessel 2 via the opening 23a or 23b. The cryopreservation device 1 of the present embodiment is surrounded by a housing (not illustrated), and the task space 3 is maintained, for example, in a dry environment with a dewpoint of −40° C. or lower, preferably, a dew point of −50° C. or lower, due to nitrogen gas or the like that has evaporated from the inside of the cryopreservation vessel 2. By covering the task space including the openings 23a and 23b of the cryopreservation vessel 2 with the housing, the risk of frostbite caused by a worker directly touching the drawer 13 and the liquid nitrogen and the risk of lack of oxygen caused by the nitrogen gas that evaporates from the openings 23a and 23b can be eliminated. Additionally, by maintaining the inside of the housing in the dry environment, dew condensation or the like within the task space 3 can be prevented.

Figure 6:
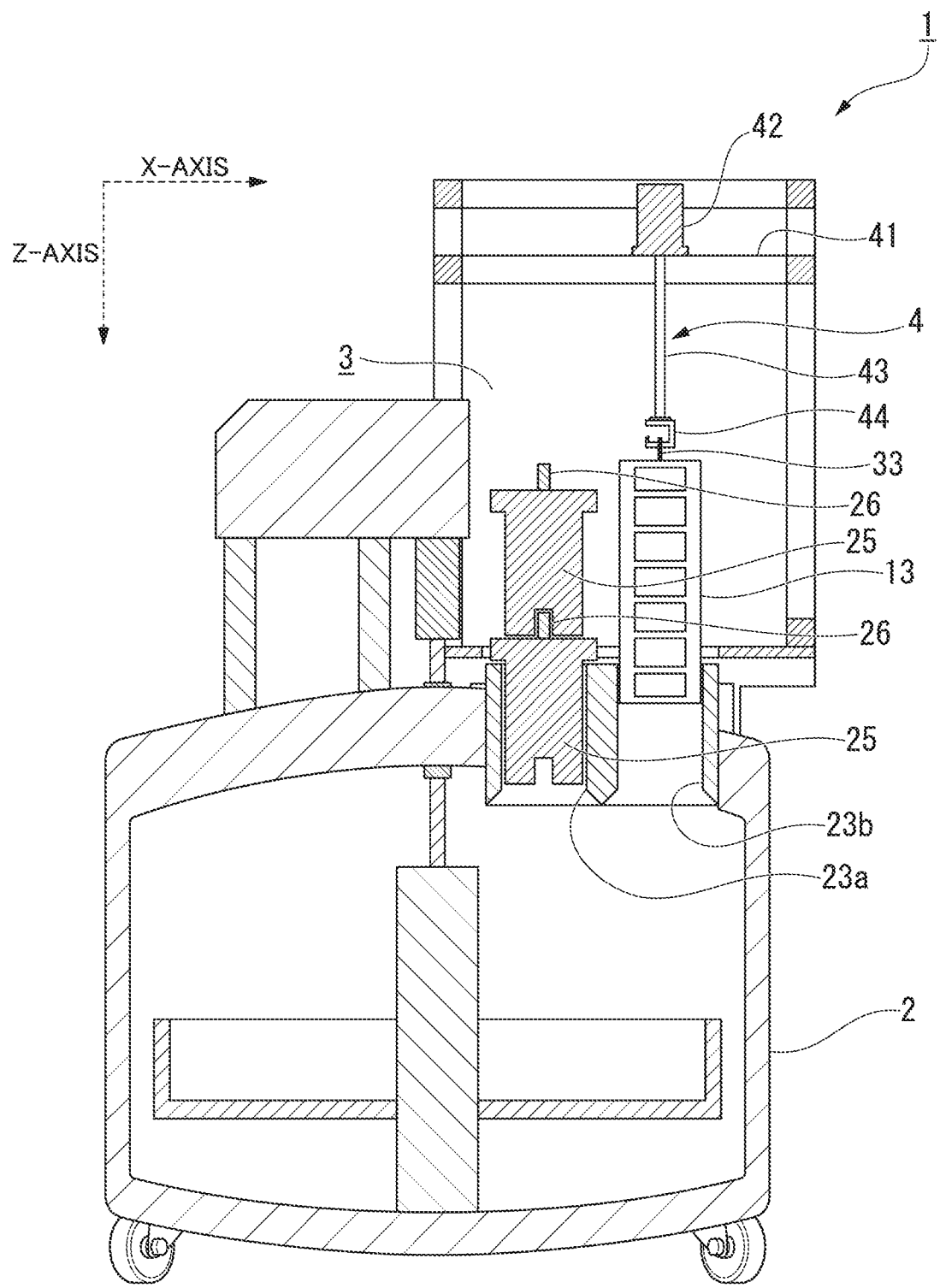
FIG. 6 is a side schematic view illustrating the operation of a drawer-raising/lowering device in the cryopreservation device of the first embodiment according to the present invention.

As illustrated in FIG. 6, the drawer-raising/lowering device 4 is a member which is configured to raise and lower the drawer 13 in the Z-axis direction via any one of the openings 23a and 23b in a state where the drawer 13 is held, for example, by gripping, and is provided within the task space 3. The drawer-raising/lowering device 4 is constituted by a support rail 41, a raising/lowering device drive part 42, a main shaft part 43, and a hook 44.

The support rail 41 is provided in the X-axis direction in an upper part of the task space 3. The raising/lowering device drive part 42 is attached to the support rail 41 so as to be movable in the X-axis direction.

The main shaft part 43 is provided at the raising/lowering device drive part 42 so as to hang down therefrom. Additionally, the hook 44 is provided at a lower end of the main shaft part 43.

The form of the main shaft part 43 is not particularly limited as long as it is possible to couple the raising/lowering device drive part 42 and the hook 44 and to hang the hook 44 down from the raising/lowering device drive part 42. For example, the main shaft part 43 may be a rod-shaped member or may be an aspect in which chains capable of being split into two or more pieces are combined together.

Additionally, the raising/lowering device drive part 42 is not particularly limited as long as the hook 44 can be raised and lowered in the Z-axis direction via the main shaft part 43, and can be appropriately selected according to the aspect of the above-described main shaft part 43. For example, in a case where the aspect of the main shaft part 43 is a rod-shaped member, a mechanism that rotates a roller member that journals the main shaft part 43 may be adopted. Additionally, in a case where the aspect of the main shaft part 43 is the combination of the chains capable of being split into two or more pieces, a mechanism having a splitting function and a winding-up function of the chains may be adopted.

The shape of the hook 44 is not particularly limited as long as the drawer 13 can be gripped. For example, a hook shape may be adopted. Accordingly, the gripping part 33 provided at an upper part of the drawer 13 can be gripped.

According to the drawer-raising/lowering device 4 configured in this way, the hook 44 can be moved to a position above any one of the opening 23a and the opening 23b corresponding to the position of a drawer 13 where an intended sample is kept by being moved on the support rail 41 in the X-axis direction.

Additionally, when the gripping part 33 provided at the upper part of the drawer 13 is gripped by lowering the drawer-raising/lowering device 4 into the cryopreservation vessel 2, the position of the hook 44 can be easily adjusted by being moved on the support rail 41 in the X-axis direction. Accordingly, even if there is only one of drawer-raising/lowering devices 4, the drawer 13 can be loaded into and unloaded from the plurality of openings 23a and 23b.

Additionally, by driving the raising/lowering device drive part 42, the hook 44 can be raised and lowered in the Z-axis direction via the main shaft part 43. That is, the drawer 13 can be raised and lowered in the Z-axis direction via any one of the openings 23a and 23b in a state where the drawer 13 is gripped. Accordingly, the drawer 13 can be loaded into and unloaded from the cryopreservation vessel 2.

Moreover, the hook 44 can be maintained at an arbitrary height in the Z-axis direction by stopping the driving of the raising/lowering device drive part 42. That is, the drawer 13 can be maintained at an arbitrary height in a state where the drawer 13 is gripped.

Figure 7:
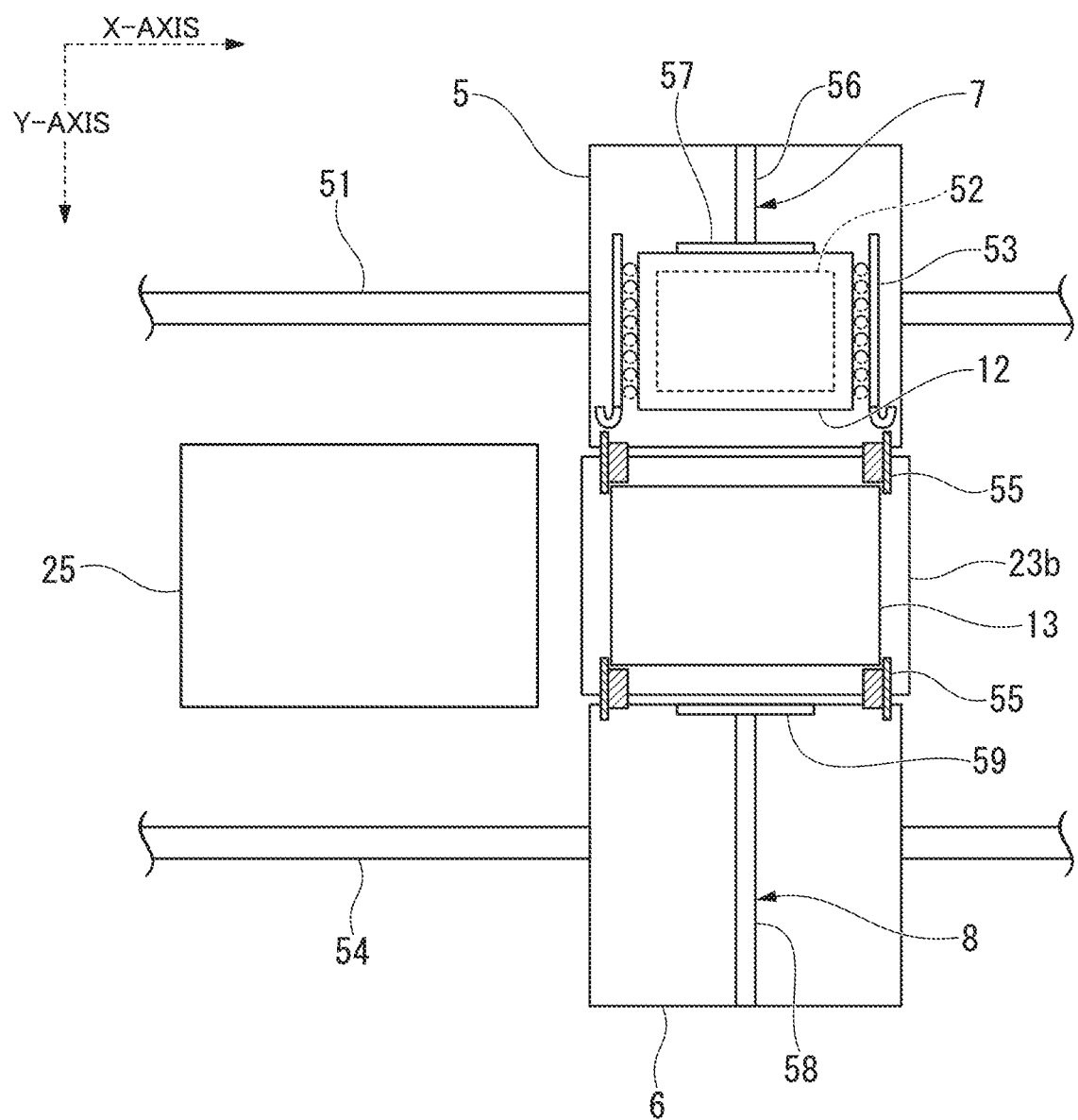
FIG. 7 is a plan schematic view illustrating a first stage, a second stage, a first pressing device, and a second pressing device in the cryopreservation device of the first embodiment according to the present invention.

As illustrated in FIG. 7, a first X-axis rail 51 is provided in the X-axis direction at the lower part of the task space 3. The first stage 5 is attached to the first X-axis rail 51, and is movable in the X-axis direction. For that reason, as seen in plan view, the first stage 5 can be moved to a position adjacent to each of the opening 23a and the opening 23b.

Since the first stage 5 is adjacent to any of the openings 23a and 23b as seen in plan view, when a desired box 12 stored at an arbitrary height is extracted from the drawer 13, it becomes unnecessary to unload the entire drawer 13 from the cryopreservation vessel 2. Accordingly, by raising the drawer 13 until a bottom surface of a storage space where the desired box 12 is stored and the first stage 5 reach the same height, only the desired box 12 can be extracted onto the first stage 5 by the second pressing device 8 (second arm) to be described below. Hence, a rise in the temperature of samples other than the intended sample can be suppressed. Moreover, since it is not necessary to pull up the entire drawer 13, the size of the device can be reduced in a height direction thereof.

The first stage 5 allows a box 12 to be placed thereon, and a portion of a placement surface is provided with the opening 52. Accordingly, each vial 11 can be pushed up from below the first stage 5 via the opening 52. Additionally, a bar code provided, for example, at a lower part of each vial 11 can be identified from below the first stage 5 via the opening 52.

The shape of the opening 52 is not particularly limited as long as the push-up of the vial 11 and the reading of the bar code are possible. For example, an opening that is slightly smaller than the box 12 by may be adopted, or a plurality of openings may be adopted in the shape of a slit or in the shape of a lattice.

Additionally, a box guide 53 is provided on the placement surface in the first stage 5. A box 12 pressed by the second pressing device 8 to be described below can be adjusted by the box guide 53 so as to be placed at a predetermined position on the first stage 5.

Additionally, a second X-axis rail 54 is provided in the X-axis direction on a side opposite to the first X-axis rail 51 with the openings 23a and 23b interposed therebetween at the lower part the task space 3. The second stage 6 is attached to the second X-axis rail 54, and is movable in the X-axis direction. For that reason, as seen in plan view, the second stage 6 can be moved to a position adjacent to each of the opening 23a and the opening 23b.

The first stage 5 and the second stage 6 are movable in the X-axis direction as described above, and are movable in the X-axis direction in a pair. Accordingly, for example, when the drawer 13 is loaded into and unloaded from the opening 23a, the first stage 5, the opening 23a, and the second stage 6 may be aligned adjacent to each other in this order. Here, a direction in which the first stage 5, the opening 23a, and the second stage 6 are aligned adjacent to each other is referred to as a "Y-axis direction". In addition, the first stage 5 and the second stage 6 are not only simultaneously movable as a pair but also are individually operable.

Drawer guides 55 are respectively provided on side surfaces of the first stage 5 and the second stage 6 on the opening 23b side. When the drawer 13 is raised or lowered in the Z-axis direction via the opening 23b, the drawer 13 can be supported so as to be sandwiched by the drawer guides 55 from both sides of the drawer 13. Accordingly, since shaking or the like of the drawer 13 can be suppressed, the raising and lowering of the drawer 13 and the movement of the box 12 between the first stage 5 and the drawer 13 can be smoothly performed.

The drawer guides 55 are not particularly limited as long as the drawer 13 can be supported. For example, the drawer 13 may be supported by causing wheels made of resin to abut against surfaces of four corners of the drawer 13 in the X-axis direction and the Y-axis direction.

The first pressing device 7 is a member configured to press the box 12 placed on the first stage 5 to the drawer 13 side, thereby storing the box 12 in the drawer 13. The first pressing device 7 is provided on the first stage 5. The first pressing device 7 is constituted by a first support part 56 and a first pressing part 57.

The first support part 56 has a base end provided on a side surface opposite to a side surface that faces the openings 23a and 23b, on the first stage 5. The first support part 56 is attached such that a tip thereof is movable in the Y-axis direction.

The first pressing part 57 is provided at the tip of the first support part 56. The box 12 can be pressed in the Y-axis direction by the first pressing part 57.

According to the first pressing device 7 configured in this way, by pressing the box 12 placed on the first stage 5 to the drawer 13 side, the box 12 can be stored in the drawer 13.

The second pressing device 8 is a member configured to press the box 12 maintained at a height adjacent to the first stage 5 using the drawer-raising/lowering device 4 to the first stage 5 side, thereby moving the box 12 onto the first stage 5. The second pressing device 8 is provided on the second stage 6. The second pressing device 8 is constituted by a second support part 58 and a second pressing part 59.

The second support part 58 has a base end provided on a side surface opposite to a side surface that faces the openings 23a and 23b, on the second stage 6. The second support part 58 is attached such that a tip thereof is movable in the Y-axis direction.

The second pressing part 59 is provided at the tip of the second support part 58. The box 12 can be pressed in the Y-axis direction by the second pressing part 59.

According to the second pressing device 8 configured in this way, by pressing the box 12 located at the height adjacent to the first stage 5 within the drawer 13 to the first stage 5 side, the box 12 can be placed on the first stage 5.

Since the first stage 5, the second stage 6, the first pressing device 7, and the second pressing device 8 operate in cooperation with each other, the box 12 is capable of being placed on the first stage 5 from the drawer 13 unloaded from the cryopreservation vessel 2 by the drawer-raising/lowering device 4. Additionally, the box 12 placed on the first stage 5 is capable of being stored in the drawer 13.

For example, in a case where the box 12 is placed on the first stage 5 from the drawer 13 after being unloaded via the opening 23b by the drawer-raising/lowering device 4, first, the first stage 5 and the second stage 6 move to positions that face each other with the opening 23b interposed therebetween as seen in plan view.

Next, the drawer 13 is unloaded via the opening 23b from the cryopreservation vessel 2 by the drawer-raising/lowering device 4, and the drawer 13 is raised until a bottom surface of a storage space where the desired box 12 is stored and the first stage 5 reach the same height. When the drawer 13 is raised, shaking of the drawer 13 is suppressed by supporting the drawer 13 using the drawer guides 55 provided on the first stage 5 and the second stage 6.

Next, by pressing the desired box 12 in the Y-axis direction using the second pressing device 8 in a state where the drawer 13 is supported, the desired box 12 is moved from the drawer 13 to the first stage 5. The desired box 12 can be placed on the first stage 5 by the operation.

A case extracted onto the first stage 5 is conveyed to the vicinity of an extraction port (not illustrated) of the housing (not illustrated) by a conveyance system 61 provided in the task space 3.

Figure 8:
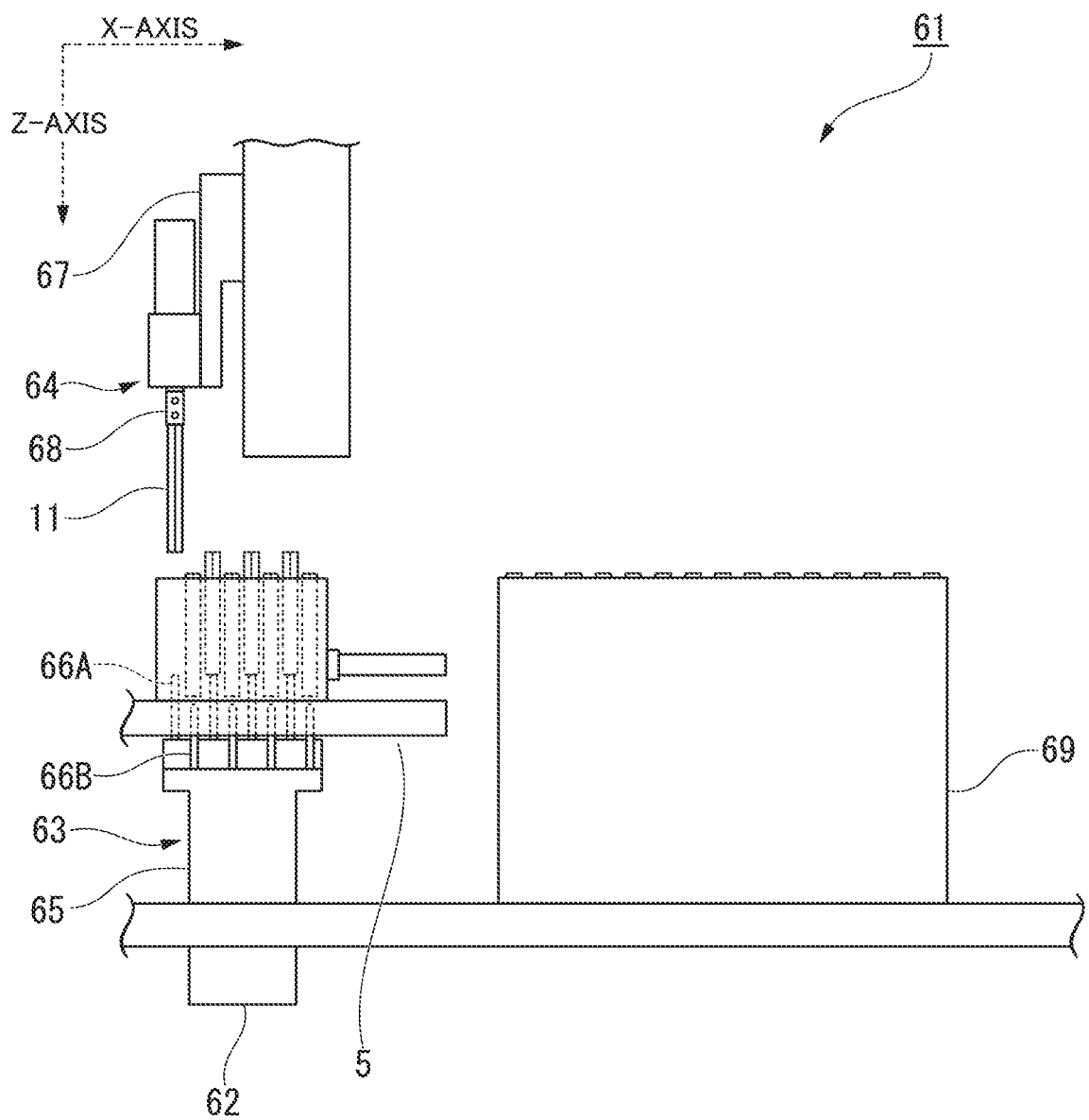
FIG. 8 is a side schematic view illustrating a conveyance system in the cryopreservation device of the first embodiment according to the present invention.

As illustrated in FIG. 8, the conveyance system 61 is roughly constituted by the first stage 5, an identification device 62, a push-up part 63, and a vial raising/lowering device 64.

The identification device 62 is a device configured to identify the vial 11 and is provided around the first X-axis rail 51 or on the first stage 5. The identification device is not particularly limited as long as the vial 11 can be identified. For example, the identification device may be any device as long as the device can recognize information on an image pasted on the vial 11, and specifically, may include a bar code reader or the like.

In a case where the identification device 62 is a bar code reader, for example, it is preferable that an identification code be provided at a lower part of the vial 11, and an opening be provided in a bottom surface of the first stage 5 and the identification device 62 be provided below the first stage 5. Accordingly, the vial 11 stored within the box 12 can be easily identified. Additionally, in this case, the identification device 62 (bar code reader) may be provided at any position between the opening 23a and the push-up part 63 on a movement path of the first stage 5 in an X-axis. In addition, in a case where the identification device 62 is a bar code reader, both of a reader capable of reading a one-dimensional bar code and a reader capable of reading a two-dimensional bar code are possible.

By providing the identification device 62, stock information, such as a keeping place and loading/unloading date and time of the vial 11, and information, such as an operation history, can be automatically recorded. Additionally, since automatic recordation is possible, even in a case where a lot of samples are treated, mistakes, such as forgetting to read, can be reduced and accidents, such as misplacement of the samples, can be prevented.

The push-up part 63 is a device configured to push up the lower part of each vial 11 accommodated within the case placed on the first stage 5 via the opening 52 provided in the first stage 5 from below the first stage 5.

The push-up part 63 is roughly constituted by, for example, a supporting base 65, and a plurality of columnar parts 66A and 66B linearly provided on the supporting base 65. The supporting base 65 is split into two units, the columnar part 66A located corresponding to an odd-numbered row among vial rows accommodated in a box row is fixed to one unit, and the columnar part 66B located corresponding to an even-numbered row among the vial rows accommodated in the box row is fixed to the other unit. Additionally, the supporting base 65 is capable of alternately raising the two units, and is capable of raising one unit, thereby simultaneously pushing up odd-numbered vials among vial rows accommodated within a box 12. Similarly, the supporting base is capable of raising the other unit, thereby simultaneously pushing up even-numbers vials among the same vial rows. In addition, since the supporting base 65 is split into the two units, and thus, the intervals between the pushed-up vials 11 are wider than those in a case where all the vials 11 are pushed up at once, a gripping part 68 of the vial raising/lowering device 64 can sufficiently ensure a space brought into an open state.

The vial raising/lowering device 64 is configured to include a Y-axis rail (not illustrated) provided in an upper part of the task space 3 of the housing (not illustrated) so as to extend in the Y-axis direction, a raising/lowering device drive part 67 provided in this Y-axis rail (not illustrated) and movable in the Y-axis direction, and the gripping part 68 provided at a lower end of the raising/lowering device drive part 67.

The raising/lowering device drive part 67 is not particularly limited as long as the raising/lowering device drive part is a mechanism capable of being raised and lowered in the Z-axis direction.

The gripping part 68 is not particularly limited as long as the gripping part is a mechanism capable of gripping the vials 11 one by one. Specifically, the gripping part may be constituted by a plurality of plate-like members provided so as to be separated from and brought close to each other. The plate-like members are moved so as to be separated from each other in order to bring the gripping part 68 into the open state, and are moved so as to be brought close to each other in order to bring the gripping part into a closed state. Accordingly, a vial 11 can be gripped in a space between the plate-like members.

According to the conveyance system 61 configured as described above, when the box 12 extracted onto the first stage 5 moves from the opening 23a to the push-up part 63, the position of the desired vial 11 is identified by the identification device 62. Thereafter, if the first stage 5 moves to the push-up part 63, a corresponding unit of the supporting base 65 is raised on the basis of the positional information obtained by the identification device 62, and thus, the desired vial 11 is pushed out upward. After the vial raising/lowering device 64 is moved to a position above the pushed-out vial 11, the gripping part 68 is lowered, and the desired vial 11 is gripped by the gripping part 68 and then conveyed to a vial place 69. Accordingly, the worker can easily extract the desired vial 11.

The input/output device 9 is, for example, a personal computer that has a display unit and an input unit that are provided outside the housing (not illustrated). The worker can operate the input/output device 9 to issue an instruction to the control device (not illustrated) built in the cryopreservation device 1, thereby performing various operations for extracting and storing the vial 11 or the box 12. For example, the worker can select a sample extracted from the stock information and issue an instruction for the extraction of the vial 11 or the box 12, thereby automatically moving the desired vial 11 or the desired box 12 to the extraction port (not illustrated). Additionally, information on the vials 11 managed in the cryopreservation device 1 can also be stored in a storage unit of the external input/output device 9.

Additionally, a control program that issues instructions for operation to the drawer-raising/lowering device 4, the first stage 5, the second stage 6, the first pressing device 7, the second pressing device 8, the identification device 62, the push-up part 63, the vial raising/lowering device 64, and the like are incorporated in the control device (not illustrated) within the cryopreservation device 1. Accordingly, for example, a movement instruction for lowering the drawer 13 using the drawer-raising/lowering device 4 and moving the drawer within the cryopreservation vessel 2 after the box 12 is placed on the first stage 5 by the second pressing device 8 can be issued. Accordingly, a rise in the temperature of other samples stored within the drawer 13 can be suppressed.

Next, a method of unloading the drawer 13 via the opening 23b and extracting a desired box 12, using the method of using the cryopreservation device 1 of the present embodiment, that is, the method of using the above-described cryopreservation device 1, will be described.

First, the input/output device 9 is operated to instruct the control device (not illustrated) to extract the desired box 12. Accordingly, the drawer table 24 rotates, and the drawer 13 that has stored the desired box 12 moves to a position immediately below the opening 23b.

Next, the drawer-raising/lowering device 4 moves in the X-axis direction, and moves to a position immediately above the opening 23b. Thereafter, the hook 44 is lowered downward along the Z-axis and grips the gripping part 26 of the cap 25. Thereafter, by raising the hook 44 upward along the Z-axis, the cap 25 is removed from the opening 23b. The cap 25 removed from the opening 23b is placed in an empty space, such as on the other cap 25 by moving the drawer-raising/lowering device 4 and the hook 44 in the X-axis direction and in the Z-axis direction.

Next, the first stage 5 and the second stage 6 are moved in the X-axis direction, and thus, move to positions where both sides of the opening 23a are sandwiched as seen in plan view. Additionally, the drawer-raising/lowering device 4 moves to a position immediately above the opening 23b from which the cap 25 is removed.

Next, the drawer 13 is unloaded via the opening 23b from the cryopreservation vessel 2 by the drawer-raising/lowering device 4, and the drawer 13 is raised until a bottom surface of a storage space where the desired box 12 is stored and the first stage 5 reach the same height. When the drawer 13 is raised, shaking of the drawer 13 is suppressed by supporting the drawer 13 using the drawer guides 55 provided on the first stage 5 and the second stage 6.

Next, by pressing the desired box 12 in the Y-axis direction using the second pressing device 8, the desired box 12 is moved from the drawer 13 to the first stage 5. The desired box 12 is placed on the first stage 5 by the operation.

Next, in order to prevent the temperature of the remaining boxes from rising, the drawer-raising/lowering device 4 is lowered, and the drawer 13 is loaded into the cryopreservation vessel 2. Thereafter, by performing an operation reverse to the operation of removing the above-described cap 25, the opening 23b is blocked by the cap 25.

Next, the box 12 is carried out to the extraction port (not illustrated) by moving the first stage 5, on which the box 12 is placed, in the X-axis direction. Then, the worker can extract the desired box 12 from the extraction port (not illustrated). The extraction operation of the box 12 is completed by the operation.

Next, a method of unloading the drawer 13 via the opening 23b and extracting the desired vial 11, using the above-described cryopreservation device 1, will be described.

First, the worker operates the input/output device 9 and instructs the control device (not illustrated) to extract the desired vial 11. Accordingly, through the same operation as the above-described extraction of the box 12, a desired drawer 13 is unloaded via the opening 23b from the cryopreservation vessel 2, and the drawer 13 is raised until a bottom surface of a storage space where the desired box 12 is stored and the first stage 5 reach the same height.

Next, by pressing the desired box 12 in the Y-axis direction using the second pressing device 8, the desired box 12 is moved from the drawer 13 to the first stage 5. The desired box 12 is placed on the first stage 5 by the operation.

Next, in order to prevent the temperature of the remaining boxes from rising, the drawer 13 is lowered until an upper surface enters the cryopreservation vessel 2, and stands by in this state. In that case, the drawer-raising/lowering device 4 maintains a state where the drawer 13 is gripped.

Next, the first stage 5 is moved up to the push-up part 63 by moving the first stage 5, on which the box 12 is placed, in the X-axis direction. When the box 12 extracted onto the first stage 5 moves from the opening 23b to the push-up part 63, the position of the desired vial 11 is identified by the identification device 62.

Next, if the first stage 5 moves to the push-up part 63, a corresponding unit of the supporting base 65 is raised on the basis of the positional information obtained by the identification device 62, and thus, the desired vial 11 is pushed out upward.

Next, after the vial raising/lowering device 64 is moved to a position above the pushed-out vial 11, the gripping part 68 is lowered, and the desired vial 11 is gripped by the gripping part 68 and then conveyed to the vial place 69. Accordingly, the worker can easily extract the desired vial 11.

The box 12 after the desired vial 11 is extracted moves in the X-axis direction while being placed on the first stage 5 and moves to a position adjacent to the drawer 13. Thereafter, the drawer 13 is raised by the drawer-raising/lowering device 4 until a bottom surface of a space where the desired box 12 within the drawer 13 is stored is aligned with the first stage 5 and the second stage 6.

Next, the box 12 is moved from the first stage 5 to the drawer 13 by pressing the box 12 in the Y-axis direction using the first pressing device 7. After the box 12 is moved, the drawer 13 is lowered and loaded into the cryopreservation vessel 2 by the drawer-raising/lowering device 4. Thereafter, by performing an operation reverse to the operation of removing the above-described cap 25, the opening 23b is blocked by the cap 25. The extraction operation of the vial 11 is completed by the operation.

Although the method of extracting a desired box 12 or a desired vial 11 has been described above, description about the method of storing the box 12 or the vial 11 will be omitted because the box or the vial can be stored by performing the operation reverse to the operation when the box or the vial is extracted.

As described above, according to the cryopreservation device 1 of the present embodiment, the cryopreservation device 1 includes the cryopreservation vessel 2 that internally accommodates the drawer 13 configured to store the vials 11 side by side in the vertical direction in each box 12 and has the opening 23a or 23b communicating with the task space 3 provided in the upper surface thereof; the drawer-raising/lowering device 4 that raises and lowers the drawer 13 in the vertical direction via the opening 23a or 23b in a state where the drawer 13 is gripped and maintains the drawer 13 at an arbitrary height; the first stage 5 that is provided above the cryopreservation vessel 2 so as to be adjacent to the opening 23a or 23b as seen in plan view and allows the box 12 to be placed thereon; and the second pressing device 8 that presses the box 12 to move the box 12 to the first stage 5.

In this way, since the first stage 5 is provided so as to be adjacent to the opening 23a or 23b as seen in plan view, only the intended sample can be extracted onto the first stage 5 by the second pressing device 8 without pulling up the entire drawer 13 from the cryopreservation vessel when the intended sample is extracted from the cryopreservation vessel 2 by the drawer-raising/lowering device 4. Hence, the intended sample can be automatically extracted, and a rise of the temperature of samples other than the intended sample can be suppressed. Moreover, since it is not necessary to pull up the entire drawer 13, the size of the device can be reduced in a height direction thereof.

Additionally, according to the cryopreservation device 1 of the present embodiment, the cryopreservation device further includes the control device (not illustrated) that controls at least the drawer-raising/lowering device 4 and the second pressing device 8. For that reason, a series of operations of lowering the drawer 13 using the drawer-raising/lowering device 4 and accommodating the drawer within the cryopreservation vessel 2 after the box 12 is placed on the first stage 5 by the second pressing device 8 can be automatically performed. Accordingly, a rise in the temperature of samples other than the intended sample can be further suppressed.

Additionally, according to the cryopreservation device 1 of the present embodiment, the cryopreservation device further includes the first pressing device 7 that presses the box 12 placed on the first stage 5 from the first stage 5 side to the drawer 13 side to store the box in the drawer 13. Accordingly, the vials 11 or the box 12 can be automatically stored in the cryopreservation vessel 2.

Additionally, according to the cryopreservation device 1 of the present embodiment, the drawer table 24 is further included in the lower part within the cryopreservation vessel 2, the drawer 13 is allowed to be placed on the circumference of each of the two arbitrary concentric circles centered on the rotary shaft 28 of the drawer table 24, and the opening 23a or 23b is configured to be located on the circumference of each of the concentric circles as seen in plan view. Accordingly, a lot of the drawers 13 can be stored within the cryopreservation vessel 2.

Additionally, according to the cryopreservation device 1 of the present embodiment, the first stage 5 and the second stage 6 adjacent to the opening 23a or 23b as seen in plan view are configured to support the drawer 13 when the drawer 13 is raised or lowered in the Z-axis direction via the opening 23a or 23b. For that reason, when the drawer 13 is raised or lowered, the vibration of the drawer 13 can be suppressed. Accordingly, the raising and lowering of the drawer 13, the movement of the box 12 between the drawer 13 and the first stage 5, or the like can be smoothly performed.

Second Embodiment

The vials 11 in which the preservation targets are accommodated are cryopreserved in the cryopreservation device of the first embodiment, whereas envelopes in which preservation targets are accommodated are cryopreserved in the present embodiment. The configuration of the cryopreservation device itself is also changed with a change in the preservation targets. Hereinafter, the cryopreservation device of the present embodiment will be described mainly in terms of differences from the first embodiment.

The envelopes are boxes that store bag-shaped preservation objects, such as blood bags or umbilical cord blood bags, therein. By using the envelopes, even if the preservation targets have an indefinite shape, the preservation targets can be easily extracted or stored, and simultaneously, the preservation targets can also be protected from a shock or the like. The envelopes may be formed of any kinds of materials as long as materials that can maintain the shape of the envelopes themselves are adopted. The envelopes may be formed of resin and may be formed of a metal with large thermal conductivity, for example, aluminum.

Additionally, it is preferable that the envelopes be provided with identification codes, similar to the vials in the first embodiment.

Figure 9:
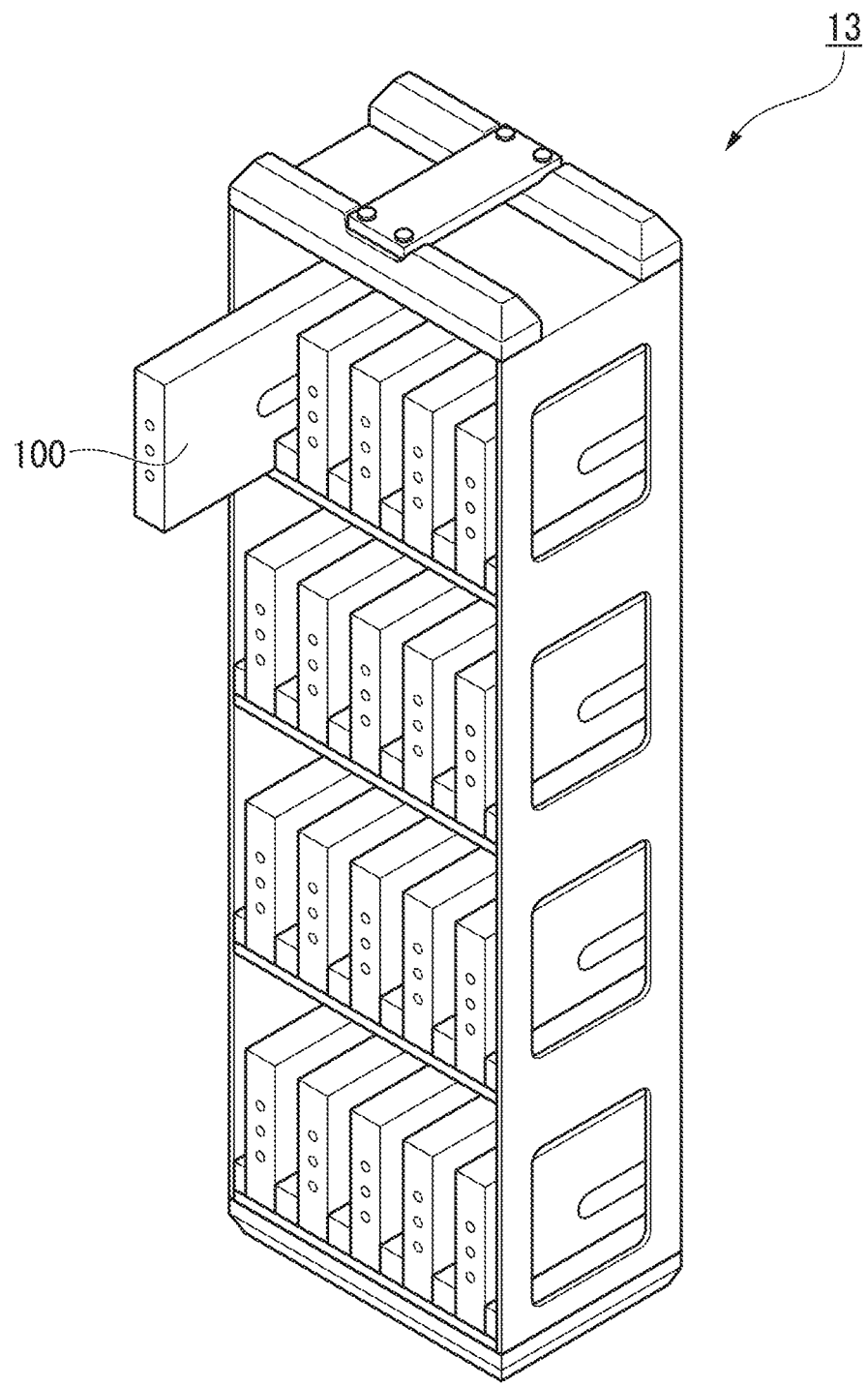
FIG. 9 is a perspective schematic view illustrating a drawer in a cryopreservation device of a second embodiment according to the present invention.

As illustrated in FIG. 9, several envelopes 100 are accommodated at regular intervals in shelves of the drawer 13 provided perpendicularly to the Z-axis direction. In FIG. 9, five envelopes 100 are accommodated upright in each of four shelves. In order to restrict the positions and postures of the envelopes 100, it is preferable that the shelves of the drawer 13 be provided with partition plates. In addition, grooves that allow the envelopes 100 to be upright may be provided instead of the partition plates.

Figure 10:
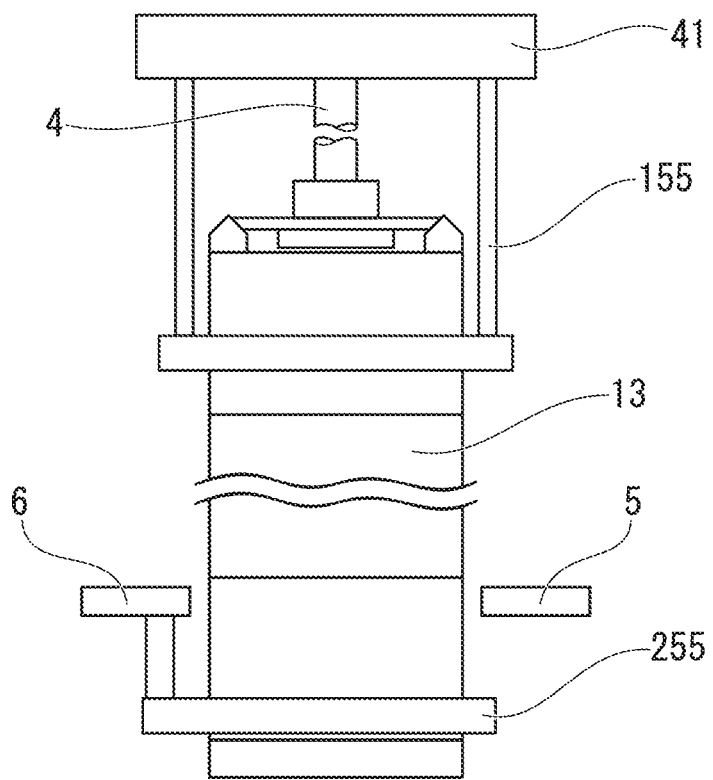
FIG. 10 is a side schematic view illustrating the drawer-raising/lowering device, the drawer, a first drawer guide, a second drawer guide, the first stage, and the second stage in the cryopreservation device of the second embodiment according to the present invention.

Additionally, in the first embodiment, in order to support the drawer 13 when the drawer 13 is raised or lowered in the Z-axis direction via the opening 23b, the drawer guides 55 are provided on the side surfaces of the first stage 5 and the second stage 6 on the opening 23b side. With respect to one of the drawer guides 55, it is preferable to use at least two drawer guides in the present embodiment. As illustrated in FIG. 10, it is preferable that the first and second drawer guides 155 and 255 be located up and down in the Z-axis direction in which the drawer 13 moves. By providing the guides in two places in this way, when the drawer 13 is raised and lowered, the positional deviation of the drawer 13 can be restricted. Hence, the drawer 13 can be raised and lowered in a more accurate posture in a more accurate place.

It is preferable that the first drawer guide 155 be provided on the support rail 41 that is a portion of the drawer-raising/lowering device 4. Accordingly, when the drawer 13 is pulled up, particularly the positional deviation of an upper part of the drawer 13 can be restricted.

The second drawer guide 255 is provided below the first drawer guide 155. Accordingly, when the drawer 13 is pulled up, particularly the positional deviation of a lower part of the drawer 13 can be restricted. It is preferable that the second drawer guide 255 be attached to the second stage 6.

Figure 11:
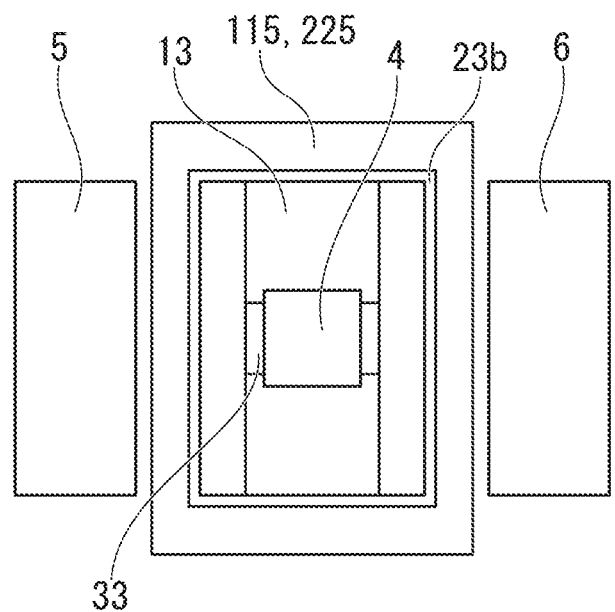
FIG. 11 is a plan schematic view illustrating the drawer-raising/lowering device, the drawer, the first drawer guide, the second drawer guide, the first stage, and the second stage in the cryopreservation device of the second embodiment according to the present invention.

As illustrated in FIG. 11, it is preferable that the first and second drawer guides 155 and 255 be provided so as to surround a periphery of the drawer 13. Accordingly, positional deviations in two directions of the X-axis direction and the Y-axis direction can be restricted. As long as the shape of the drawer 13 is a quadrangular prism, it is preferable that the shape of the first and second drawer guides 155 and 255 be a square frame shape.

Figure 12:
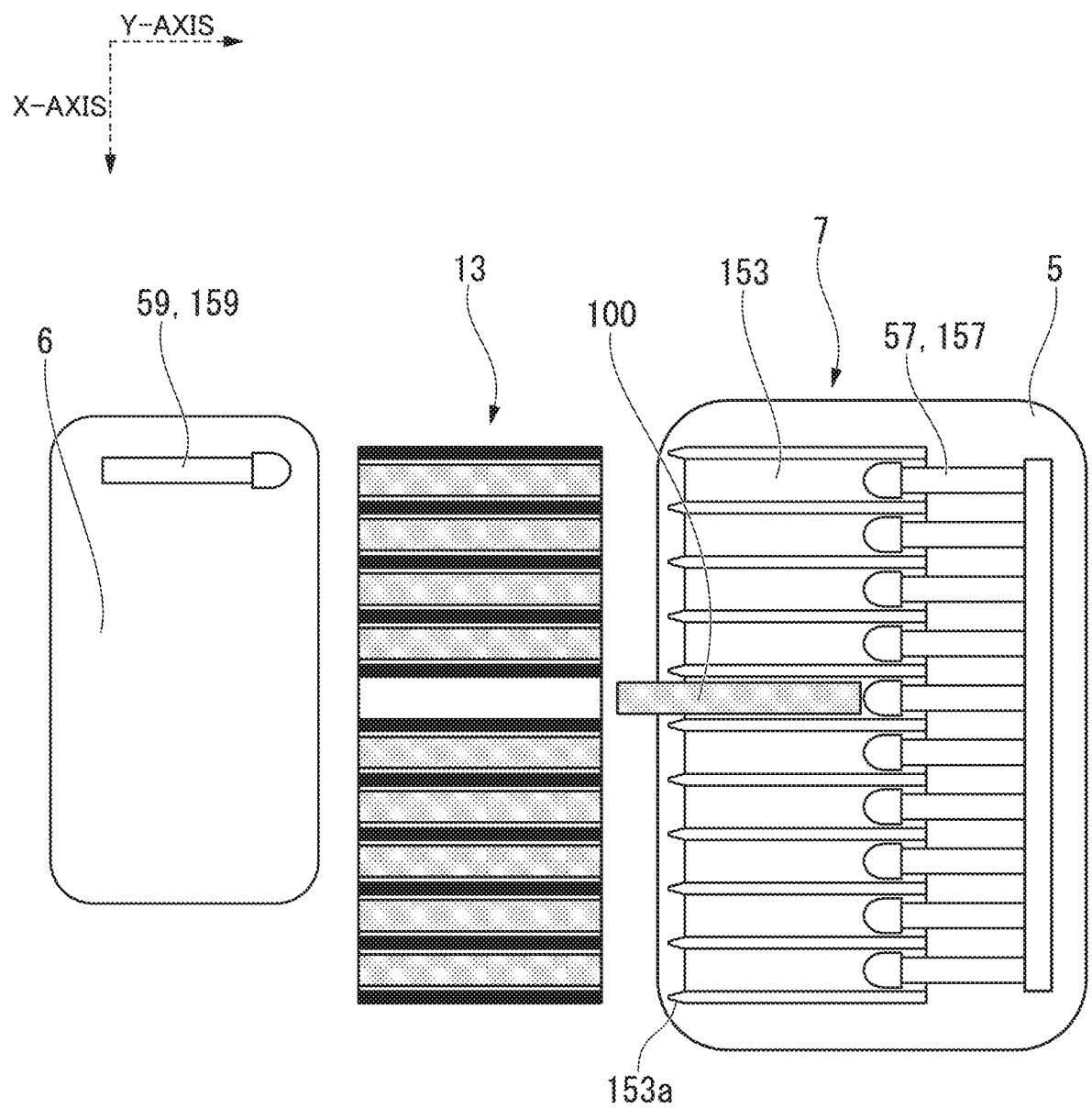
FIG. 12 is a plan schematic view illustrating the operation of the first pressing device and the second pressing device in the cryopreservation device of the second embodiment according to the present invention.

The cryopreservation device of the first embodiment has the first pressing device 7 and the second pressing device 8, and the first and second pressing devices 7 and 8 have the first and second support parts 56 and 58, and the first and second pressing parts 57 and 59, respectively. In contrast, in the cryopreservation device of the present embodiment, as illustrated in FIG. 12, the first pressing device 7 further includes an envelope holder 153. Additionally, the first pressing part 57 of the first pressing device 7 is provided with a plurality of pressing arms 157 . . . . In contrast, the second pressing part 59 of the second pressing device is provided with one pressing arm 159.

One second pressing arm 159 that is the pressing part 59 provided in the second pressing device can move in the X-axis direction on the second stage 6, and press a specific envelope 100 within the drawer 13 located at a height adjacent to the first stage 5 to the first stage 5 side, to place the specific envelope on the first stage 5. That is, at least a tip of the second pressing arm 159 has a size such that the tip can push out one envelope 100.

In addition, in the present embodiment, there is one of the second pressing arm 159. However, it is possible to provide a plurality of the pressing arms. In this case, a plurality of envelopes 100 can be simultaneously pushed out.

As described above, the first pressing device 7 has the envelope holder 153. Additionally, the first pressing part 57 of the first pressing device 7 is provided with the plurality of pressing arms 157 . . . .

As illustrated in FIG. 12, partition plates are provided in the envelope holder 153 so as to correspond to the partition plates provided in the shelves of the drawer 13. That is, the partition plates are provided such that the envelopes 100 accommodated in the drawer 13 can be accommodated. Moreover, tapers are formed at ends 153a of the partition plates of the envelope holder 153 that faces the partition plates provided in the drawer 13. Accordingly, the envelope holder 153 can be accurately arranged with respect to the drawer 13.

Additionally, the first pressing arm 157 has a plurality of arms that pass through spaces between the partition plates that are provided in the envelope holder 153. Accordingly, even if an envelope 100 is accommodated in any portion of the envelope holder 153, the envelope 100 can be accommodated in the drawer 13 by pushing out the first pressing arm 157 toward the drawer 13 without taking the position of the envelope into consideration. Moreover, even in a case where there are a plurality of the envelopes 100, the envelopes can be accommodated in the drawer 13 at once. In addition, the first pressing arm 157 can also have only one pressing arm, similar to the second pressing arm 159. In that case, the pressing arm 157 can move in the X-axis direction on the first stage 5.

Additionally, in the cryopreservation device of the present embodiment, the extraction port of the housing that covers the task space 3 may be provided with an automatic door, and the first stage 5 may be moved on the X-axis in conjunction with this automatic door so as to be an automatic sliding door. In this case, the worker can extract the envelope 100 without putting his/her hand into the housing.

Next, a method of unloading a drawer 13 via the opening 23b and extracting a desired envelope 100, using the above-described cryopreservation device 1, will be described.

First, similar to the first embodiment, the worker operates the input/output device 9 and instructs the control device (not illustrated) to extract the desired envelope 100. Accordingly, the drawer 13 is raised via the opening 23b until a bottom surface of a storage space where the desired envelope 100 is stored and the first stage 5 reach the same height. In this case, since the first and second drawer guides 155 and 255 are provided up and down in the Z-axis direction in which the drawer 13 moves, the drawer 13 can be moved to a predetermined position in a predetermined posture.

Next, the second pressing arm 159 of the second pressing device 8 moves in the X-axis direction, and faces the desired envelope 100. Next, by pressing the desired envelope 100 in the Y-axis direction, the second pressing arm 159 moves only the desired envelope 100 from the drawer 13 to the envelope holder 153 on the first stage 5. The desired envelope 100 is placed on the envelope holder 153 by the operation.

Next, the first stage 5 on which the envelope holder 153 loaded with the envelope 100 is placed is moved in the X-axis direction, and moves up to the extraction port of the housing that covers the task space 3. The worker can put his/her hand into the housing from the extraction port of the housing to extract the envelope 100. In addition, in a case where the automatic sliding door is provided, the worker can extract the envelope 100 without putting his/her hand into the housing. The extraction operation of the desired envelope 100 is completed by the operation.

Hereinafter, a method of accommodating the envelope 100 in the cryopreservation device will be described.

First, the input/output device 9 is operated to move the first stage 5, on which the envelope holder 153 is placed, up to an accommodation port. In addition, this accommodation port can also be used as the extraction port. Next, the worker accommodates the envelope 100 in a designated place of the envelope holder 153. This designated place is designated on the basis of a loading and unloading situation by the input/output device 9.

Next, the first stage 5 on which the envelope holder 153 is placed is moved in the X-axis direction and is made adjacent to the opening 23b. In this case, the drawer 13 moves such that the first stage 5 and a bottom surface of a shelf of a drawer to be accommodated reach the same height.

Next, the first pressing arm 157 of the first pressing device 7 is moved in the Y-axis direction and abuts against the envelope 100 on the envelope holder 153. Thereafter, the envelope 100 is further pushed out, and if the entire envelope 100 is accommodated in the drawer 13, the movement of the envelope is stopped. Accordingly, the envelope 100 is accommodated in the drawer 13.

In this case, since the first pressing arm 157 includes the plurality of arms, the envelope 100 can be reliably accommodated in the drawer through single push-out even if the envelope 100 is accommodated in any place of the envelope holder 153. Additionally, even a plurality of the envelopes 100 can be accommodated through single push-out. Thereafter, the drawer 13 is accommodated in the cryopreservation vessel, similar to the first embodiment.

According to the cryopreservation device of the present embodiment, the cryopreservation device includes the cryopreservation vessel 2 that internally accommodates the drawer 13 configured to store the envelopes 100 in several stages side by side in the vertical direction and has the opening 23a or 23b communicating with the task space 3 provided in the upper surface thereof; the drawer-raising/lowering device 4 that raises and lowers the drawer 13 in the vertical direction via the opening 23a or 23b in a state where the drawer 13 is gripped and maintains the drawer 13 at an arbitrary height; the first stage 5 that is provided the cryopreservation vessel 2 so as to be adjacent to the opening 23a or 23b as seen in plan view and allows the envelope holder 153 capable of accommodating the envelopes 100 to be placed thereon; and the second pressing device 8 that presses the envelopes 100 to move the envelope holder 153 on the first stage 5.

For this reason, the same effects as the cryopreservation device of the first embodiment can be obtained.

Additionally, in the cryopreservation device of the present embodiment, it is preferable that the first and second drawer guides 155 and 255 be provided in two places up and down in the Z-axis direction in which the drawer 13 is raised and lowered. For this reason, the positional deviation of the drawer 13 in the X-axis and Y-axis directions can be restricted. In the present embodiment, in order to extract only a predetermined envelope 100 among the plurality of envelopes 100 placed on the shelves of the drawer 13, high accuracy is required for the position of the envelope 100. If the first and second drawer guides 155 and 255 are provided, this is preferable because the positional deviation of the drawer 13 in the X-axis and Y-axis directions can be further restricted. Moreover, if the first and second drawer guides 155 and 255 are provided up and down in the Z-axis direction, this is preferable because inclination or shaking that may be caused when the drawer 13 is raised and lowered can also be restricted.

Additionally, in the cryopreservation device of the present embodiment, the first pressing device 7 further includes the envelope holder 153, the first pressing part 57 has the plurality of pressing arms 157, and the second pressing part 59 has the one second pressing arm 159. The second pressing arm 159 can move on the second stage 6 in the X-axis direction and push out only the desired envelope in the direction of the first stage 5. A storage space corresponding to the plurality of envelopes 100 accommodated in the drawer 13 is provided in the envelope holder 153 included in the first pressing device 7. Additionally, the envelope holder 153 is arranged such that the storage space thereof and the storage space of the drawer 13 coincide with the Y-axis direction. For this reason, the envelopes 100 accommodated in the drawer 13 can be accommodated in the envelope holder 153 on the first stage 5 by pushing out the second pressing arm 159 in the Y-axis direction.

Moreover, the first arm 157 has a plurality of arms, and the arms are located corresponding to the envelopes 100 accommodated in the drawer. Hence, even if an envelope 100 to be accommodated in the cryopreservation vessel 2 is accommodated at any position of the envelope holder 153, the envelope 100 can be reliably accommodated in the drawer 13 by single movement of the first pressing arm 157. Additionally, even if there are a plurality of envelopes 100 to be accommodated, these envelopes can be accommodated in the drawer 13 by moving the first pressing arm 157 once.

Moreover, if the automatic sliding door is provided in the housing in which the task space 3 is partitioned, the worker can extract an envelope 100, without putting his/her hand into the cryopreservation device.

Although the embodiments of the present invention have been described above in detail with reference to the drawings, specific configuration is not limited to these embodiments, and designs not departing from the scope of the present invention are also included.

For example, an example in which the drawers 13 are concentrically aligned in two stages within the cryopreservation vessel 2 and include the two openings 23a and 23b has been described in the above-described cryopreservation device 1. However, the present invention is not limited to this embodiment. For example, a drawer 13 may be arranged in one arbitrary circle within the cryopreservation vessel 2 and one opening may be provided, or drawers 13 may be arranged in three or more arbitrary concentric circles within the cryopreservation vessel 2 and three or more openings may be provided.

Additionally, although an example in which the input/output device 9 is provided outside the housing (not illustrated) has been described in the above-described cryopreservation device 1, the present invention is not limited to this embodiment. For example, one or both of the input unit and the display unit of input/output device 9 may be configured integrally with the cryopreservation device, such as by being provided on the outer wall of the housing.

Additionally, although a case in which the control program, which issues instructions for operation to the drawer-raising/lowering device 4, the first stage 5, the second stage 6, the first pressing device 7, the second pressing device 8, the identification device 62, the push-up part 63, the vial raising/lowering device 64, and the like, is incorporated into the control device (not illustrated) built in the cryopreservation device 1 and the worker operates the input/output device 9 connected to the outside and thus issues various instructions to the control unit has been described in the above-described cryopreservation device 1, the present invention is not limited to this embodiment. For example, the worker may directly instruct respective operation parts, such as the drawer-raising/lowering device 4, by operating the control device (not illustrated) instead of interposing the input/output device 9.

Additionally, although an example in which the first stage 5 and the second stage 6 interlock with each other has been described in the above-described cryopreservation device 1, the present invention is not limited to this embodiment, and a configuration in which the first stage and the second stage move separately may be adopted.

Additionally, although a case where the preservation targets are the vials 11 or the envelopes 100 consisting of a vessel and a lid has been described in the above-described cryopreservation device 1, the present invention is not particularly limited as long as arbitrary shapes capable of being stored in the drawer 13, such as a tube shape, are provided.

INDUSTRIAL APPLICABILITY

The cryopreservation device of the present invention is available as a device configured to cryopreserve biological samples, such as sperms, fertilized ova, and cells of laboratory animals.

REFERENCE SIGNS LIST

1: CRYOPRESERVATION DEVICE
2: CRYOPRESERVATION VESSEL
3: TASK SPACE
4: DRAWER-RAISING/LOWERING DEVICE (FIRST ARM)
5: FIRST STAGE
6: SECOND STAGE
7: FIRST PRESSING DEVICE (THIRD ARM)
8: SECOND PRESSING DEVICE (SECOND ARM)
9: INPUT/OUTPUT DEVICE
11: VIAL (PRESERVATION TARGET)
12: BOX (UNIT)
13: DRAWER (CASE)
21: INNER TANK
22: OUTER TANK
23a, 23b: OPENING
24: DRAWER TABLE (ROTARY TABLE)
25: CAP
26: GRIPPING PART
27: MOTOR
28: ROTARY SHAFT
29: DRAWER GUIDE
31: VERTICAL PLATE
32: FLOOR PLATE
33: GRIPPING PART
41: SUPPORT RAIL
42: RAISING/LOWERING DEVICE DRIVE PART
43: MAIN SHAFT PART
44: HOOK
51: FIRST X-AXIS RAIL
52: OPENING
53: BOX GUIDE
54: SECOND X-AXIS RAIL
55: DRAWER GUIDE
56: FIRST SUPPORT PART
57: FIRST PRESSING PART
58: SECOND SUPPORT PART
59: SECOND PRESSING PART
61: CONVEYANCE SYSTEM
62: IDENTIFICATION DEVICE
63: PUSH-UP PART
64: VIAL RAISING/LOWERING DEVICE
65: SUPPORTING BASE
66A, 66B: COLUMNAR PART
67: RAISING/LOWERING DEVICE DRIVE PART
68: GRIPPING PART
69: VIAL PLACE
100: ENVELOPE
155: FIRST DRAWER GUIDE
255: SECOND DRAWER GUIDE
159: SECOND PRESSING ARM (SECOND PRESSING PART)
157: FIRST PRESSING ARM (FIRST PRESSING PART)
153: ENVELOPE HOLDER
153a: TAPERED PART

The invention claimed is:
1. A cryopreservation device comprising:
a case, wherein the case is configured to store boxes side by side in a vertical direction in the case, the boxes being configured to store vials, or wherein the case is configured to accommodate several boxes at regular intervals in shelves of the case, the boxes being configured to store bag-shaped preservation objects;
wherein the case has two opposite open vertical side surfaces;
a cryopreservation vessel configured to internally accommodate the case having an opening communicating with an outside provided in an upper surface thereof;
a first arm configured to raise and lower the case in a vertical direction via the opening in a state where the case is held and to maintain the case at an arbitrary height;

a first stage that is provided above the cryopreservation vessel so as to be adjacent to the opening as seen in plan view and allows the preservation targets to be placed thereon; and a second arm configured to move a desired one of the boxes from the case to the first stage via the open vertical side surface facing the first stage, when the bottom surface of a storage space in the case, where the desired box is stored, is located at the same height as the first stage.

2. The cryopreservation device according to claim 1, wherein the cryopreservation device further comprises a control unit that controls at least the first arm and the second arm.

3. The cryopreservation device according to claim 1, wherein the cryopreservation device further comprises a third arm configured to move the box placed on the first stage to the case.

4. The cryopreservation device according to claim 3, wherein the cryopreservation device further comprises a rotary table at a lower part within the cryopreservation vessel,
wherein a drawer guide is provided to allow the case to be placed on the circumference of a predetermined circle centered on a rotary shaft of the rotary table, and
wherein the opening is located on the circumference of the circle as seen in plan view.

5. The cryopreservation device according to claim 4, wherein two or more of the openings are provided on an upper surface of the cryopreservation vessel so as to be adjacent to each other in a radial direction of the rotary table,
wherein two or more drawer guides are provided on the rotary table to allow the case to be placed on the circumference of each of two or more predetermined concentric circles centered on the rotary shaft of the rotary table, and
wherein the openings are located on the circumference of each of the concentric circles as seen in plan view.

6. The cryopreservation device according to claim 5, wherein the first arm, the second arm and the first stage are movable in a respective direction orthogonal to the direction from the open side surface facing the first stage toward the first stage side, and wherein the second arm and third arm are movable along the direction from the open side surface facing the first stage toward the first stage side.

7. The cryopreservation device according to claim 3, wherein a tip part of the third arm is provided with a plurality of pressing arms,
wherein the second arm is provided with one pressing arm, the one pressing arm being movable on the second stage in a direction from the second stage to the open vertical side surface of the case facing the second stage, and
wherein the first stage is further provided with a holder having a space into which the plurality of pressing arms are inserted.

8. The cryopreservation device according to claim 7, wherein the holder is provided with a partition plate configured to partition the space into which the plurality of pressing arms are inserted.

9. The cryopreservation device according to claim 7, wherein the cryopreservation device further comprises a guide that restricts a positional deviation when the case is raised and lowered in the vertical direction, and
wherein the guide has a first guide located up along a lifting and lowering direction of the case, and a second guide located below the first guide.

10. The cryopreservation device according to claim 9, wherein the cryopreservation device further comprises a second stage provided opposite to the first stage across the opening at a position adjacent to the opening, as seen in plan view, the cryopreservation vessel,
wherein the first guide is attached to the first arm, and wherein the second guide is attached to the second stage.

11. The cryopreservation device according to claim 8, wherein a tip part of the partition plate is provided with a taper.

12. The cryopreservation device according to claim 1, wherein the cryopreservation device further comprises a second stage provided opposite to the first stage across the opening at a position adjacent to the opening, as seen in plan view, above the cryopreservation vessel.

13. The cryopreservation device according to claim 12, wherein the first stage and the second stage are movable in a pair in the direction orthogonal to the direction from the case side toward the first stage side.

14. The cryopreservation device according to claim 12, wherein the first stage and the second stage adjacent to the opening as seen in plan view support the case when the case is raised or lowered in the vertical direction via the opening.

15. The cryopreservation device according to claim 1, wherein the cryopreservation device further comprises an identification device configured to identify a vial placed on the first stage or configured to identify a box configured to store a bag-shaped preservation object placed on the first stage.

* * * * *